United States Patent [19]

Komai et al.

[11] 4,169,848
[45] Oct. 2, 1979

[54] POLYMERIC DIACYL PEROXIDES

[75] Inventors: Takeshi Komai; Masaru Matsushima, both of Chita, Japan

[73] Assignee: Nippon Oil and Fats Co., Ltd., Tokyo, Japan

[21] Appl. No.: 909,125

[22] Filed: May 24, 1978

[30] Foreign Application Priority Data

May 31, 1977 [JP] Japan ................................ 52-62812

[51] Int. Cl.$^2$ ................................................ C07C 69/76
[52] U.S. Cl. ........................ 260/453 RZ; 260/453 R
[58] Field of Search ..................... 260/453 R, 453 RZ

[56] References Cited

U.S. PATENT DOCUMENTS

| 3,232,922 | 2/1966 | Guillet et al. | 260/453 R |
| 3,991,109 | 11/1976 | D'Angelo et al. | 260/453 R |

OTHER PUBLICATIONS

H. U. Pechman et al., Ber. der Deuchen Chemishen Gesershaft 27, 1510–1513 (1894).
N. A. Milas et al., J. Amer. Chem. Soc., 68, 534, 1946.
N.S. Tsvetkov et al., Chem. Abst, 59, 7651a.
N. S. Tsvetkov et al., Chem. Abst. 64, 15989g.
N. S. Tsvetkov et al., Chem. Abst., 64, 5293d.
N. S. Tsvetkov et al., Chem. Abst., 60, 10892e.
N. S. Tsvetkov et al., Chem. Abst., 67, 54445a.
N. S. Tsvetkov et al., Chem. Abst., 84, 136,120f.
T. Sugimura, Jour. Chem. Soc. of Japan, 69, 4 718–721 (1966), (Industrial Chemistry Section).
E. Ott, Org. Sym. Coll. II, 528, (1943).
H. Fever et al., Org. Syn. Coll. IV, 554, (1963).
H. Staudinger, Ber 41, 3563, (1908).
V. Auger, Anal. Chem., [6], 22, 347 (1891).
W. H. Perkin, J. Chem. Soc., 53, 563, (1888).
E. E. Blaise, Bull. Soc. Chein France [4]5, 687, (1909).

Primary Examiner—John M. Ford
Assistant Examiner—Robert C. Whittenbaugh
Attorney, Agent, or Firm—Blanchard, Flynn, Thiel, Boutell & Tanis

[57] ABSTRACT

Polymeric diacyl peroxides containing ester groups in the molecules are insensitive to impact, friction and heat. Accordingly, they can be safely produced and handled. They are useful as industrial polymerization initiators and they dissolve promptly in vinyl-type monomers.

11 Claims, No Drawings

POLYMERIC DIACYL PEROXIDES

BACKGROUND OF THE INVENTION

1. Field of the Invention

This invention relates to organic polymeric peroxides containing ester groups in the molecules which can be used as free radical polymerization initiators for vinyl-type monomers.

2. Description of the Prior Art

Polymeric diacyl peroxides which are obtained by reacting dibasic acid chlorides with sodium peroxide are known.

For example, H. V. Pechman et. al. report in Bericht Der Deuchen Chemichen Gesselshaft 27, 1510 (1894) that polymeric diacyl peroxides are obtained from phthalic acid chloride and sodium peroxide.

N. A. Milas et. al. disclose in J. Amer. Chem. Soc. 68, 534 (1946) that oxalic acid chloride is reacted with sodium peroxide, thereby obtaining the corresponding polymeric diacyl peroxide.

Further, N. S. Tsvetkov et. al. report in Chem. Abst. 60, 5293d (1964) and ibid 60, 10892e (1964) that aliphatic dibasic acid chlorides are reacted with sodium peroxide whereby some kinds of polymeric diacyl peroxides having the following formula are obtained:

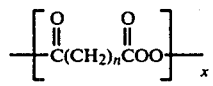

wherein n is 2–10 and x is 16–35.

It has been known that the above-mentioned polymeric diacyl peroxides are useful as polymerization initiators for vinyl monomers.

For example, N. S. Tsvetkov et.al. disclose in Chemical Abstracts 67, 54,445a (1967) that when these peroxides are used as the polymerization initiator, the molecular weight of the thus-obtained polymer was twice that of the polymer produced when benzoyl peroxide was used.

A. Ya. Sorkin et.al. disclose in Chemical Abstracts 84, 136120f (1976) that when these peroxides were used as the polymerization initiator for vinyl acetate, the resultant polymers had larger molecular weights and fewer branches in the molecule, in comparison with that obtained by using benzoyl peroxide.

Sugimura et.al. report in Japan Technical Chemistry 69, 718 (1966) that styrene-methyl methacrylate graft-polymer was obtained by using poly(phthaloyl peroxide).

As described in the foregoing, a polymeric diacyl peroxide is a useful polymerization initiator but it has the following defects:

(1) It is an explosive compound which is sensitive to impact, friction and heat. (refer to Chemical Abstracts 59, 7651a (1963)).

(2) It cannot be used as an industrial polymerization initiator, since its solubility in an organic solvent and vinyl-type monomers is low. (refers to Japan Industrial Chemistry 69, 718 (1966) and Chem. Abst. 64, 15989g (1966).

SUMMARY OF THE INVENTION

A main object of the present invention is to provide polymeric diacyl peroxides which are useful as industrial polymerization initiators.

A further object of the invention is to provide polymeric diacyl peroxides which can be safely produced and handled. This invention is based on the knowledge that organic compounds which are obtained by incorporating ester groups in the molecule of a polymeric diacyl peroxide are different in many point from the known polymeric dicyl peroxide, accomplishing the object of the present invention.

The compounds obtained by the inventors have the following formula.

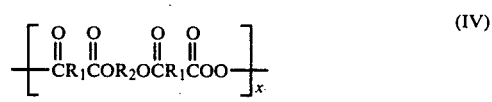

(wherein $R_1$ is alkylene having 1–15 carbon atoms, or phenylene, $R_2$ is alkylene having 2–10 carbon atoms, $-(CH_2)_2O(CH_2)_2-$, $-(CH_2)_2O(CH_2)_2O(CH_2)_2-$

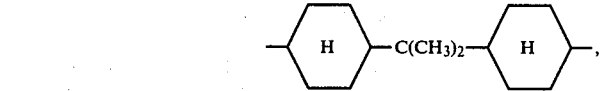

and x is 2–20).

$R_1$ is, for example, $-CH_2-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-(CH_2)_{13}-$, $-(CH_2)_{14}-$, $-(CH_2)_{15}-$,

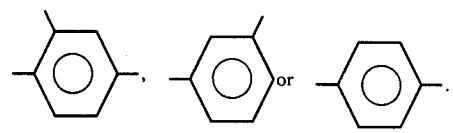

$R_2$ includes $-(CH_2)_2-$, $-CH(CH_3)CH_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_2O(CH_2)_2-$, $-(CH_2)_2O(CH_2)_2-$,

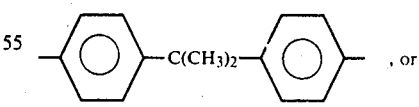

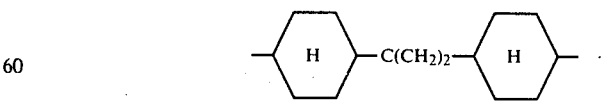

The peroxides of the present invention may be produced according to a process comprising reacting a dicaboxylic acid chloride (I) and a glycol (II), within a stream of dried air or dried nitrogen gas, with subjecting to dehydrochlorination, thereby obtaining an acid chloride containing ester groups in the molecular (III), adding the obtained acid chloride (III) into a solution of sodium peroxide little by little with stirring to react the two, and filtering The obtained product may be separated from the filtrate easily by filtering and may be dried by being placed in the air or under reduced pressure.

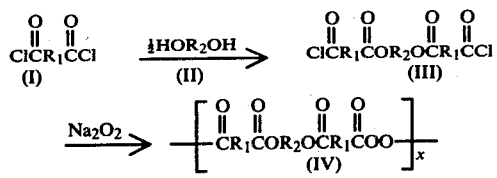

($R_1$, $R_2$ and x are the same as described in the foregoing)

The reaction of compound (I) with compund (II) may be carried out at atmospheric pressure.

However it is preferable for advancing the reaction smoothly and shortening the reaction time to perform the reaction at a reaction pressure at 40–50 mm Hg using a water jet pump and removing the resulting hydrogen chloride out of the reaction system.

The reaction time is preferably 0.5–3 hours. The mole ratio of compound (I) to compound (II) must be 2:1.

When compound (I) and/or compound in (II) are compounds which at least one of $R_1$ and $R_2$ have a large number of carbon atoms in the molecule, the resultant compound (III) is solid.

Accordingly, the reaction is preferably carried out in a solvent such as toluene and the like.

The reaction of compound (III) with sodium peroxide may be carried out according to the almost the same procedure as that used in producing the conventional diacyl peroxide. The reaction temperature is −10°–30° C., preferably 0°–10° C. and the reaction time is 0.25–3 hours, preferably 0.5–1.5 hours. The mole ratio of compound (III) to sodium peroxide is 1:1–2, preferably 1:1–1.5. The concentration of the sodium peroxide aqueous solution is 1–15 wt%, preferably 2–5 wt%.

Illustrative of the dicarboxylic acid chlorides are aliphatic dicarboxylic acid chlorides such as chlorides of methanedicarboxylic acid (malonic acid), 1,2-ethanedicarboxylic acid (succinic acid), 1,3-propanedicarboxylic acid (glutaric acid), 1,4-butanedicarboxylic acid (adipic acid), 1,5-pentanedicarboxylic acid (pimelic acid), 1,6-hexanedicarboxylic acid (suberic acid), 1,7-heptanedicarboxylic acid (azelaic acid) 1,8-Octanedicarboxylic acid (sebacic acid), 1,9-nonanedicarboxylic acid, 1,10-decanedicarboxylic acid, 1,11-undecanedicarboxylic acid, 1,12-dodecanedicarboxylic acid, 1,13-tridecanedicarboxylic acid, 1,14-tetradecanedicarboxylicacid, 1,15-pentadecanedicarboxylicacid and aromatic dicarboxylic acid chlorides such as chlorides of phthalic acid, isophthalic acid and terephthalic acid.

As the glycols used in the present invention, there are mentioned ethylene glycol, propylene glycol, trimethylene glycol, 1,4-butanediol, 1,5-pentanediol, 1,6-hexanediol, 1,7-heptanediol, 1,8-octanediol, 1,9-nonanediol, 1,10-decanediol, diethylene glycol, triethylene glycol, 2,2-bis(4-hydroxyphenyl)propane and 2,2-bis(4-hydroxcyclohexyl)propane.

The polymeric diacyl peroxides containing ester groups in their molecules of the present invention, compared with the conventional polymeric diacyl peroxides, are less sensitive to impact, friction and heat so that there is less risk of explosion.

They also have a high solubility in organic solvents.

Accordingly, the polymeric diacyl peroxides of the present invention are safe in the production and handling thereof and when they are added as a polymerization initiator into a vinyl type monomer, they are so promptly dissolved into it that they are used industrially without decreasing the working efficiency.

Table 1.

| | Test Results for Safety (1) | | |
|---|---|---|---|
| Peroxide | Decomposition temperature (°C.) | Impact Test (cm) | Friction test (kg/cm²) |
| The present invention $+[-C(CH_2)_4CO(CH_2)_4OC(CH_2)_4COO-]_{5.5}$ | 98 | 50 | 700 up |
| $+[-C(CH_2)_4CO(CH_2)_2O(CH_2)_2OC(CH_2)_4COO-]_{4.7}$ | 90 | 50 | 700 up |
| $+[-C(CH_2)_{10}CO(CH_2)_2OC(CH_2)_{10}COO-]_{2.6}$ | 104.5 | 60 up | 700 up |
| $+[-C(CH_2)_{10}CO(CH_2)_2O(CH_2)_2OC(CH_2)_{10}COO-]_{2.8}$ | 106 | 60 up | 700 up |
| Conventional peroxide $+[-C(CH_2)_4COO-]_{6.5}$ | 87 | 10 | 250 |
| $+[-C(CH_2)_{10}COO-]_{7.1}$ | 95 | 15 | 460 |

Test Results for Safety (2)

Ballistic mortar test    Pressure

Table 1.-continued

| Peroxide | | (based on) TNT % | vessel test (mm) | Explosibility |
|---|---|---|---|---|
| The present invention | $\left[-\text{C}(\text{CH}_2)_4\overset{\text{O}}{\overset{\|}{\text{C}}}\text{O}(\text{CH}_2)_4\overset{\text{O}}{\overset{\|}{\text{C}}}(\text{CH}_2)_4\overset{\text{O}}{\overset{\|}{\text{C}}}\text{OO}-\right]_{5.5}$ | 5.2 | 1.2 | none |
| | $\left[-\text{C}(\text{CH}_2)_4\overset{\text{O}}{\overset{\|}{\text{C}}}\text{O}(\text{CH}_2)_2\text{O}(\text{CH}_2)_2\text{O}\overset{\text{O}}{\overset{\|}{\text{C}}}(\text{CH}_2)_4\overset{\text{O}}{\overset{\|}{\text{C}}}\text{OO}-\right]_{4.7}$ | 4.6 | 1.0 under | none |
| | $\left[-\text{C}(\text{CH}_2)_{10}\overset{\text{O}}{\overset{\|}{\text{C}}}\text{O}(\text{CH}_2)_2\text{O}\overset{\text{O}}{\overset{\|}{\text{C}}}(\text{CH}_2)_{10}\overset{\text{O}}{\overset{\|}{\text{C}}}\text{OO}-\right]_{2.6}$ | 2.1 | 1.0 under | none |
| | $\left[-\text{C}(\text{CH}_2)_{10}\overset{\text{O}}{\overset{\|}{\text{C}}}\text{O}(\text{CH}_2)_2\text{O}(\text{CH}_2)_2\text{O}\overset{\text{O}}{\overset{\|}{\text{C}}}(\text{CH}_2)_{10}\overset{\text{O}}{\overset{\|}{\text{C}}}\text{OO}-\right]_{2.8}$ | 2.0 | 1.0 under | none |
| Conventional peroxide | $\left[-\overset{\text{O}}{\overset{\|}{\text{C}}}(\text{CH}_2)_4\overset{\text{O}}{\overset{\|}{\text{C}}}\text{OO}-\right]_{6.5}$ | 21.5 | 6.8 | occur |
| | $\left[-\overset{\text{O}}{\overset{\|}{\text{C}}}(\text{CH}_2)_{10}\overset{\text{O}}{\overset{\|}{\text{C}}}\text{OO}-\right]_{7.1}$ | 18.9 | 4.9 | occur |

*A testing method for "safety degree" was measured according to that described in Kitagawa et. al., "safety engineering" 4 (2) 131 (1965) and ibid. 7 (2) 171 (1968)

Table 2

| | | Solubility (25° C. g/ 100g solvent) | | | |
|---|---|---|---|---|---|
| Peroxide | | Benzene | Toluene | Styrene | Chloroform |
| The present invention | $\left[-\text{C}(\text{CH}_2)_4\overset{\text{O}}{\overset{\|}{\text{C}}}\text{O}(\text{CH}_2)_4\text{O}\overset{\text{O}}{\overset{\|}{\text{C}}}(\text{CH}_2)_4\overset{\text{O}}{\overset{\|}{\text{C}}}\text{OO}-\right]_{5.5}$ | 14.8 | 5.4 | 5.7 | 40.1 |
| | $\left[-\text{C}(\text{CH}_2)_{10}\overset{\text{O}}{\overset{\|}{\text{C}}}\text{O}(\text{CH}_2\text{O}\overset{\text{O}}{\overset{\|}{\text{C}}}(\text{CH}_2)_{10}\overset{\text{O}}{\overset{\|}{\text{C}}}\text{OO}-\right]_{2.6}$ | 10.7 | 3.1 | 5.1 | 35.5 |
| | $\left[-\text{C}(\text{CH}_2)_{10}\overset{\text{O}}{\overset{\|}{\text{C}}}\text{O}(\text{CH}_2)_2\text{O}(\text{CH}_2)_2\text{O}\overset{\text{O}}{\overset{\|}{\text{C}}}(\text{CH}_2)_{10}\overset{\text{O}}{\overset{\|}{\text{C}}}\text{OO}-\right]_{2.8}$ | 24.1 | 11.0 | 9.8 | 46.3 |
| Conventional material | $\left[-\overset{\text{O}}{\overset{\|}{\text{C}}}(\text{CH}_2)_4\overset{\text{O}}{\overset{\|}{\text{C}}}\text{OO}-\right]_{6.5}$ | 1.0 | 0.4 | 0.3 | 8.9 |
| | $\left[-\overset{\text{O}}{\overset{\|}{\text{C}}}(\text{CH}_2)_{10}\overset{\text{O}}{\overset{\|}{\text{C}}}\text{OO}-\right]_{7.1}$ | 1.9 | 1.0 | 0.5 | 10.0 |

The safety degree of the peroxides of the present invention are shown in Table 1, compared with that of the conventional polymeric diacyl peroxides.

The testing methods therefor were carried out according to that described by Kitagawa et. al. in Safety Engineering 4(2) 131 (1965), and ibid 7 (2) 171 (1968).

It is apparant from Table 1 that the peroxides of the present invention are so insensitive to impact, friction and heat without being explosive, in constrast to the known polymeric diacyl peroxides, that they are easily produced and handled.

The solubilities of the peroxides of the present invention and the known polymeric diacyl peroxides in organic solvents are shown in Table 2.

It will be understood from Table 2 that the peroxides of the present invention possess much higher solubilities in organic solvents than the known polymeric diacyl peroxides and that the peroxides of the present invention are convenient for processing in the industrial utilization thereof, since they dissolve into vinyl type monomers promptly, when they are added as polymerization initiators into the vinyl-type monomers.

The polymeric diacyl peroxides containing ester groups therein are useful as polymerization initiators for vinyl type monomers.

Illustrative vinyl type monomers are the following; ethylene, vinyl chloride, vinyl acetate, acrylonitrile, vinylidene chloride, esters of acrylic acid and styrene.

When the peroxides of the present invention are used for polymerization of monomers such as styrene, the obtained polystyrene has about twice the molecular weight of that obtained by using benzoyl peroxide or lauroyl peroxide.

PREFERRED EMBODIMENTS OF THE INVENTION

EXAMPLE 1

37 g (0.2 mole) of adipic acid chloride (purity: 99%) and 6.2 g (0.1 mole) of ethylene glycol were added into a four neck flask which was equipped with a mechanical stirrer. The contents of the flask were allowed to continue the reaction for 30 minutes while introducing dried nitrogen gas at a temperature of 25°–30° C.

The reaction system was kept under reduced pressure of 40–50 mm Hg during the reaction with evacuation of the gas contents therein by a water jet pump. After the reaction, 35 g of adipic acid chloride containing ester groups in the molecule, which was a colorless viscous liquid, was obtained. (purity: 99.5%, yield: 98.0%)

7.5 g (0.11 mole) of 50% hydrogen peroxide aqueous solution and 208 g (0.26 mole) of 5% sodium hydroxide aqueous solution were mixed to prepare an aqueous solution of sodium peroxide.

35 g of the aforementioned acid chloride was charged little by little into the obtained sodium peroxide aqueous solution at 0°–5° C. while being stirred.

The resulting mixture was kept at the same temperature for 30 minutes while being stirred and the obtained solid product was separated by filtration. It was washed with water twice and was dried under reduced pressure to obtain 25 g of white solid. At the last step, the obtained white crystals were dissolved into 50 ml of chloroform and the resulted solution was charged into 500 ml of methanol thereby recrystallizing the same. Then it was dried under reduced pressure to obtain 20 g of white solid product.

It was confirmed that the thus obtained white solid product had the following properties and was the polymeric diacyl peroxide containing ester groups in the molecule and having the following formula.

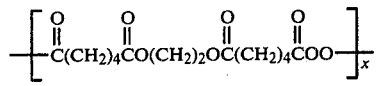

The molecular weight was measured by VPO (Hitachi Manufacturing Co., Ltd.; Molecular weight measuring apparatus No. 115).

| | |
|---|---|
| Purity determined by iodometry | 92.1% |
| Decomposition temperature | 96° C. |
| Molecular weight | 1739 (x ≈ 5.5) |
| The infrared absorption spectrum | 1725 cm$^{-1}$ (—C=O bond of ester group) |
| | 1780 cm$^{-1}$ and 1805 cm$^{-1}$ (—C=C=O group of diacyl group) |
| | 875 cm$^{-1}$ (—O—O—bond) |
| Nuclear magnetic resonance spectrum | 1.76 ppm (8H) |
| | 2.44 ppm (8H) |
| | 4.32 ppm (4H) |

EXAMPLE 2

The same procedure as described in Example 1 was carried out except that 7.6 g (0.1 mole) of propylene glycol was used in place of ethylene glycol thereby obtaining 20.5 g of the white solid product. It was recognized that the obtained white solid product had the following properties and was identified as the polymeric diacyl peroxide containing ester group in the molecule and having the following formula.

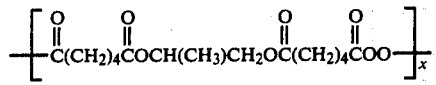

| | |
|---|---|
| Purity determined by iodometry | 96.5% |
| Decomposition temperature | 99° C. |
| Molecular weight | 1477 (x ≈ 4.4.) |
| Infrared absorption spectrum | 1725 cm$^{-1}$ (—C=O bond of ester group) |
| | 1780 cm$^{-1}$ and 1805 cm$^{-1}$ (—C=O bond of diacyl group) |
| | 880 cm$^{-1}$ (—O—O—bond) |
| Nuclear magnetic resonance spectrum | 1.80 ppm (8H) |
| | 2.44 ppm (8H) |
| | 4.15 ppm (2H) |
| | 5.20 ppm (1H) |
| | 1.28 ppm (3H) |

EXAMPLE 3

The same procedure as that described in Example 1 was carried out except that 9 g (0.1 mole) of 1,4-butanediol was used instead of ethylene glycol whereby 22 g of the white solid product was obtained. It was recognized that the obtained white solid product had the following properties and was identified as the polymeric diacyl peroxide containing ester groups in the molecule and having the following formula.

| | |
|---|---|
| Purity determined by iodometry | 94.2% |
| Decomposition temperature | 98° C. |
| Molecular weight | 1886 (x ≈ 5.5) |
| Infrared absorption spectrum | 1725 cm$^{-1}$ (—C=O bond of ester group) |
| | 1780 cm$^{-1}$ and 1805 cm$^{-1}$ (—C=O bond of diacyl group) |
| | 880 cm$^{-1}$ (—O—O bond) |
| Nuclear magnetic resonance spectrum | 1.72 ppm (12H) |
| | 2.40 ppm (8H) |
| | 4.14 ppm (4H) |

EXAMPLE 4

The same procedure as described in Example 1 was carried out except that 11.8 g (0.1 mole) of 1,6-hexanediol was used in place of ethylene glycol thus obtaining 22 g of the white solid product. It was recognized that the obtained white solid product had the following properties and was identified as the polymeric diacyl peroxide containing ester group in the molecule and having the following formula.

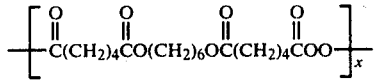

| | |
|---|---|
| Purity determined by iodometry | 97.8% |
| Decomposition temperature | 98° C. |
| Molecular weight | 2467 (x ≈ 6.6) |
| Infrared absorption spectrum | 1725 cm$^{-1}$ (—C=O bond of ester group) |
| | 1780 cm$^{-1}$ and 1805 cm$^{-1}$ |

| | |
|---|---|
| | (—C=O bond of diacyl group) |
| | 880 cm⁻¹ (—O—O—bond) |
| Nuclear magnetic resonance spectrum | 1.75 ppm (16H) |
| | 2.40 ppm (8H) |
| | 4.12 ppm (4H) |

EXAMPLE 5

The same procedure as that described in Example 1 was carried out except that 10.6 g (0.1 mole) of diethylene glycol was used in place of ethylene glycol thereby obtaining 23 g of a white solid product. The obtained white solid product had the following properties and was identified as the polymeric diacyl peroxide containing ester groups in the molecules and having the following formula.

$$\left[ -C(CH_2)_4 \overset{O}{\underset{\|}{C}} O(CH_2)_2 O(CH_2)_2 O \overset{O}{\underset{\|}{C}} (CH_2)_4 COO - \right]_x$$

| | |
|---|---|
| Purity determined by iodometry | 98.5% |
| Decomposition temperature | 90° C. |
| Molecular weight | 1680 ( x ≈ 4.7 ) |
| Infrared absorption spectrum | 1725 cm⁻¹ ( —C=O bond of ester group ) |
| | 1780 cm⁻¹ and 1805 cm⁻¹ |
| | ( —C=O bond of diacyl group ) |
| | 870 cm⁻¹ ( —O—O bond ) |
| Nuclear magnetic resonance spectrum | 1.76 ppm ( 8H ) |
| | 2.44 ppm ( 8H ) |
| | 4.28 ppm ( 4H ) |
| | 3.72 ppm ( 4H ) |

EXAMPLE 6

53.6 g (0.62 mole) of decanedicarboxylic acid chloride (purity: 99.7%), 6.2 g (0.1 mole) of ethylene glycol and 125 g of toluene were charged into a four neck flask which was equipped with a mechanical stirrer and a reflux condenser. The contents of the flask were allowed to continue the reaction for 60 minutes at a temperature of 70°–75° C. while introducing dried nitrogen gas therein, thus obtaining 171.4 g of toluene solution of 1,10-decanedicarboxylic acid chloride containing ester groups in the molecule which is a colorless liquid. (the content of the acid chloride: 32.86%)

Next, an aqueous solution of sodium peroxide was prepared with 7.5 g (0.11 mole) of 50 wt % aqueous solution of hydrogen peroxide and 208 g (0.26 mole) of 5 wt% aqueous solution of sodium hydroxide. Into this solution, 171.4 g of the toluenic solution of the acid chloride which was obtained by the aforementioned reaction was added little by little at a temperature of 0°–5° C. while being stirred.

The resulting mixture was reacted for 30 minutes while keeping same at the same temperature and the resulting creamy mixture was poured into 1000 ml of methanol, thereby crystallizing the obtained product. The crystallized product was separated by filtration and was washed with water twice and further was dried under reduced pressure thus obtaining 35 g of white solid product. The white solid product were purified according to the same procedure as that described in Example 1 whereby 30 g of white solid product was obtained.

The white solid product was examined thus showing the following properties and was confirmed to be the polymeric diacyl peroxide containing ester groups in the molecule and having the following formula.

$$\left[ -C(CH_2)_{10} \overset{O}{\underset{\|}{C}} O(CH_2)_2 O \overset{O}{\underset{\|}{C}} (CH_2)_{10} COO - \right]_x$$

| | |
|---|---|
| Purity determined by iodometry | 98.18% |
| Decomposition temperature | 104.5° C. |
| Molecular weight | 1257 ( x ≈ 2.6 ) |
| Infrared absorption spectrum | 1730 cm⁻¹ (—C=O bond of ester group) |
| | 1775 cm⁻¹ and 1800 cm⁻¹ |
| | ( C=O bond of diacyl group ) |
| | 870 cm⁻¹ ( —O—O bond ) |
| Nuclear magnetic resonance spectrum | 1.72 ppm ( 32H ) |
| | 2.44 ppm ( 8H ) |
| | 4.31 ppm ( 4H ) |

EXAMPLE 7

A mixture of 53.6 g (0.2 mole) of 1,10-decanedicarboxylic acid chloride (purity 99.7%), 10.6 g (0.1 mole) of diethylene glycol and 100 g of toluene was reacted at a temperature of 70°–75° C. for 60 minutes while introducing dried nitrogen gas according to the same procedure as that described in Example 6, whereby 153.1 g of toluenic solution of 1,10-decanedicarboxylic acid chloride containing ester groups in the molecule, which is a colorless liquid, was obtained (the content of acid chloride: 38.83%)

The toluenic solution was purified according to the same procedure as in Example 6, thus obtaining 35 g of a white solid product. The white solid product was examined thus showing the following properties and was confirmed as the polymeric diacyl peroxide containing ester groups in the molecule and having the following formula.

$$\left[ -C(CH_2)_{10} \overset{O}{\underset{\|}{C}} O(CH_2)_2 O(CH_2)_2 O \overset{O}{\underset{\|}{C}} (CH_2)_{10} COO - \right]_x$$

| | |
|---|---|
| Purity determined by iodometry | 97.69% |
| Decomposition temperature | 106° C. |
| Molecular weight | 1480 ( x ≈ 2.8 ) |
| Infrared absorption spectrum | 1730 cm⁻¹ (—C=O bond of ester group) |
| | 1775 cm⁻¹ and 1800 cm⁻¹ |
| | (—C=O bond of diacyl group) |
| | 870 cm⁻¹ (—O—O group) |
| Nuclear magnetic resonance spectrum | 1.72 ppm ( 32H ) |
| | 2.44 ppm ( 8H ) |
| | 4.27 ppm (4H ) |
| | 3.71 ppm ( 4H ) |

EXAMPLE 8

A mixture of 40.6 g (0.2 mole) of isophthalic acid chloride (purity 99.9%), 22.8 g (0.1 mole) of 2,2-bis (4-hydroxyphenyl) propane and 150 g of toluene was reacted for 2 hours at a temperature of 70°–75° C. while blowing dried nitrogen gas according to the same procedure as that described in Example 6, whereby 202 g of a toluenic solution of isophthalic acid chloride containing ester groups in the molecule, which is colorless liquid, was obtained. The content of the acid chloride was 27.49%.

The toluene solution was purified according to the same procedure as that described in Example 6, thus obtaining 32.5 g of a white solid product.

The obtained white product was examined as mentioned in the foregoing showing the following properties and was confirmed as the polymeric diacyl peroxide containing ester groups in the molecule and having the following formula

EXAMPLE 9

The same procedure as that described in Example 8 was applied except that 24.0 g (0.1 mole) of 2,2-bis(4 hydroxycyclohexyl) propane was used in place of 2,2-bis(4 hydroxyphenyl) propane, whereby 33.7 g of a white solid product was obtained.

The thus white solid product was examined showing the following properties and was confirmed to be the polymeric diacyl peroxide containing ester groups in the molecule and having the following formula.

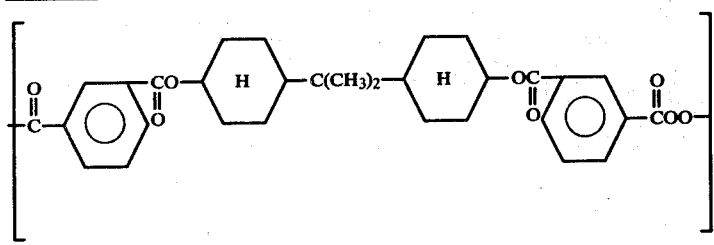

| | |
|---|---|
| Purity determined by iodometry | 96.78% |
| Decomposition temperature | 122° C. |
| Molecular weight | 1910 ($x \approx 3.6$) |
| Infrared absorption spectrum | 1720 cm$^{-1}$ (C=O bond of ester group) |
| | 1770 cm$^{-1}$ and 1790 cm$^{-1}$ (C=O bond of diacyl group) |
| | 865 cm$^{-1}$ (O—O bond) |

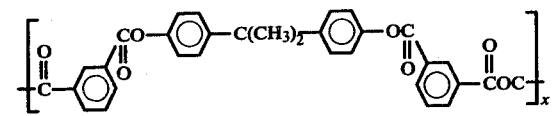

| | |
|---|---|
| Purity determined by iodemetry | 97.52 % |
| Decomposition temperature | 120° C. |
| Molecular weight | 1829 ($x \approx 3.5$) |
| Infrared absorption spectrum | 1720 cm$^{-1}$ (C=O bond of ester group) |
| | 1770 cm$^{-1}$ and 1790 cm$^{-1}$ (C=O bond of diacyl group) |
| | 865 cm$^{-1}$ (—O—O bond) |

EXAMPLE 10—Polymerization of Styrene (Bulk polymerization)

5 ml of each solution which was adjusted to an initial concentration of 0.015 mole/l of the respective peroxides as shown in Table 3, with styrene, was enclosed in respective ampules having an of inside diameter of 12 mm and was subjected to the polymerization reaction at a temperature of 80° C. for 2 hours.

After the reaction was over, each resulting solution was taken and dissolved into 50 ml of benzene. Each obtained solution was dropped into 500 ml of methyl alcohol thereby depositing the white precipitate of polystyrene. Each white precipitate was dried and weighed to calculate the respective polymerization conversion ratio.

Table 3

| Polymerization initiator | | Polymerization conversion ratio (%) | Mean molecular weight of polystyrene ($\times 10^5$) |
|---|---|---|---|
| Examples of the present invention | $+[-C(CH_2)_4CO(CH_2)_4OC(CH_2)_4COO-]_{5.5}$ | 26.86 | 1.38 |
| | $+[-C(CH_2)_{10}CO(CH_2)_2O(CH_2)_2OC(CH_2)_{10}COO-]_{2.8}$ | 26.51 | 1.03 |
| | [structure with bisphenol A diester diacyl peroxide]$_{3.6}$ | 24.61 | 1.15 |
| Comparative | Benzoyl peroxide | 25.83 | 0.63 |

Table 3-continued

| | Polymerization initiator | Polymerization conversion ratio (%) | Mean molecular weight of polystyrene ($\times 10^5$) |
|---|---|---|---|
| examples | Lauroyl peroxide | 32.57 | 0.54 |

Table 4

| | Polymerization initiator | Polymerization conversion ratio (%) | Mean molecular weight of polystyrene ($\times 10^5$) |
|---|---|---|---|
| Present invention | $\left[\begin{array}{c}\overset{O}{\underset{\|}{C}}(CH_2)_4\overset{O}{\underset{\|}{C}}(CH_2)_4O\overset{O}{\underset{\|}{C}}(CH_2)_4\overset{O}{\underset{\|}{C}}OO\end{array}\right]_{5.5}$ | 24.91 | 2.32 |
| | $\left[\begin{array}{c}\overset{O}{\underset{\|}{C}}(CH_2)_{10}\overset{O}{\underset{\|}{C}}O(CH_2)_2O(CH_2)_2O\overset{O}{\underset{\|}{C}}(CH_2)_{10}\overset{O}{\underset{\|}{C}}OO\end{array}\right]_{2.8}$ | 25.17 | 2.05 |
| | (structure with phenylene-C(CH₃)₂-phenylene groups)₃.₆ | 23.15 | 2.19 |
| Comparative example | Benzoyl peroxide | 22.73 | 0.94 |
| | Lauroyl peroxide | 30.56 | 0.84 |

The viscosity of the benzene solution of each white precipitate at 30° C. was measured whereby the mean molecular weight of the respective polystyrenes was obtained.

The obtained results are shown in Table 3.

EXAMPLE 11—Polymerization of Styrene (Suspension Polymerization)

A mixture of 5 ml of each solution which was adjusted to an initial concentration of 0.01 mole/l of respective peroxides used as a polymerization initiator as shown in Table 4, with styrene and 10 ml of 0.1 wt% aqueous solution of polyvinyl alcohol, was enclosed in respective ampule having 20 mm of an inside diameter of 20 mm.

These were placed into a shaking type oil bath and were subjected to the polymerization reaction at 75° C. for 3 hours while being shaken 60 times per minute. The thus obtained respective solutions were dropped into 300 ml of methylalcohol thereby depositing white precipitates of polystyrene. The respective obtained white precipitates were treated according to the same procedure as that described in Example 10 whereby to obtain the respective polymerization conversion ratio and the mean molecular weight of the respective polystyrene.

The obtained results are shown in Table 4.

It will be apparent from Table 3 and Table 4 that the peroxides of the present invention were more active and doubled the mean molecular weight of the obtained polystyrene in comparision with benzoyl peroxide and lauroyl peroxide which are used in commercial practice and act as polymerization initiators.

The embodiments at the invention in which an exclusive property or privilege is claimed are as follows:

1. A compound having the formula

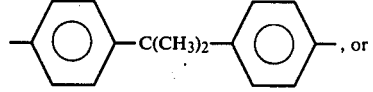

wherein $R_1$ is alkylene having 1 to 15 carbon atoms or phenylene, $R_2$ is alkylene having 2 to 10 carbon atoms, —(CH₂)₂O(CH₂)₂—, —(CH₂)₂O(CH₂)₂O(CH₂)₂—,

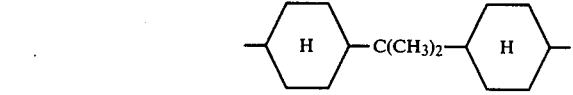

and X is a number of from 2 to 20.

2. A compound according to claim 1, having the following formula:

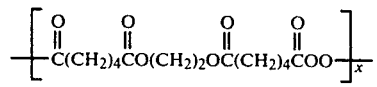

3. A compound according to claim 1, having the following formula:

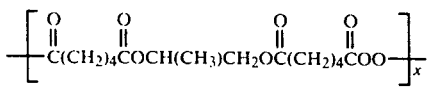

4. A compound according to claim 1, having the following formula:

5. A compound according to claim 1, having the following formula:

6. A compound according to claim 1, having the following formula:

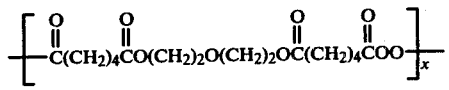

7. A compound according to claim 1, having the following formula:

8. A compound according to claim 1, having the following formula:

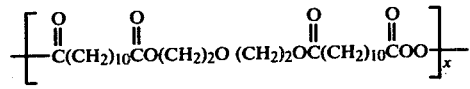

9. A compound according to claim 1, having the folllowing formula:

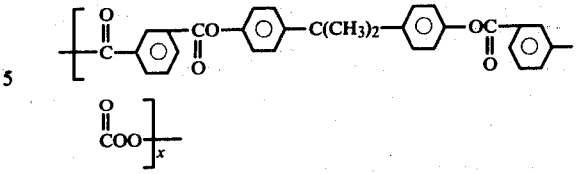

10. A compound according to claim 1, having the following formula:

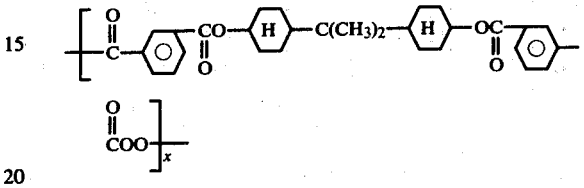

11. A process for producing a compound having the following formula (IV) which comprises reacting a dicarboxylic acid chloride of the formula (I) with a glycol of the formula (II) within a stream of dried air or dried nitrogen gas whereby an acid chloride of the formula (III) containing ester groups in the molecule is obtained, dropping the thus-obtained acid chloride (III) into an aqueous solution of sodium peroxide and reacting the two and separating the thus-obtained product from the reaction mixture,

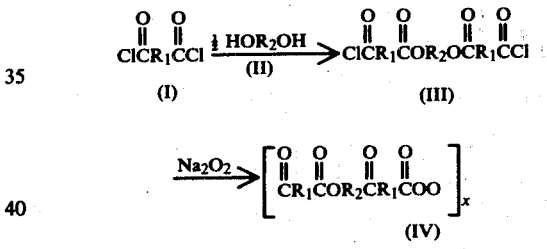

wherein $R_1$ is alkylene having 1 to 15 carbon atoms or phenylene, $R_2$ is alkylene having 2 to 10 carbon atoms, $-(CH_2)_2O(CH_2)_2-$, $-(CH_2)_2O(CH_2)_2O(CH_2)_2-$,

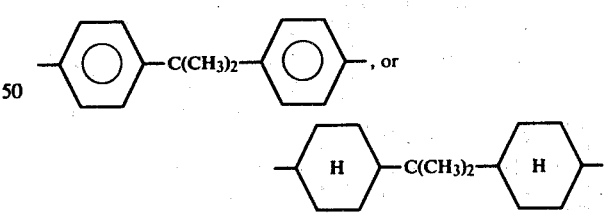

and x is a number of from 2 to 20.

* * * * *

UNITED STATES PATENT AND TRADEMARK OFFICE
CERTIFICATE OF CORRECTION

PATENT NO. : 4 169 848
DATED : October 2, 1979
INVENTOR(S) : Takeshi Komai et al It is certified that error appears in the above-identified patent and that said Letters Patent are hereby corrected as shown below:

Column 15, line 17; please correct the formula to read as follows:

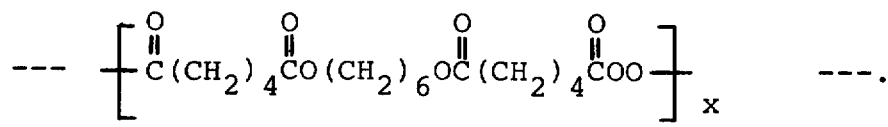

Column 16, line 40; please correct the formula to read as follows:

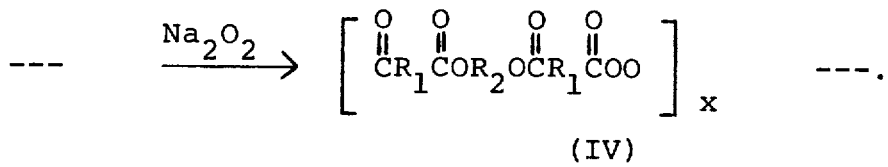

(IV)

Signed and Sealed this

Fifteenth Day of January 1980

[SEAL]

Attest:

SIDNEY A. DIAMOND

Attesting Officer    Commissioner of Patents and Trademarks